United States Patent
Feldman et al.

(10) Patent No.: US 9,126,046 B2
(45) Date of Patent: Sep. 8, 2015

(54) NEUROSTIMULATION SYSTEM FOR ENABLING MAGNETIC FIELD SENSING WITH A SHUT-DOWN HALL SENSOR

(71) Applicant: BOSTON SCIENTIFIC NEUROMODULATION CORPORATION, Valencia, CA (US)

(72) Inventors: Emanuel Feldman, Simi Valley, CA (US); Jordi Parramon, Valencia, CA (US); Joseph M. Bocek, Seattle, WA (US); Kiran Gururaj, Valencia, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 232 days.

(21) Appl. No.: 13/926,833

(22) Filed: Jun. 25, 2013

(65) Prior Publication Data

US 2013/0345777 A1 Dec. 26, 2013

Related U.S. Application Data (60) Provisional application No. 61/664,061, filed on Jun. 25, 2012.

(51) Int. Cl.
*A61N 1/08* (2006.01)
*A61N 1/36* (2006.01)
(Continued)

(52) U.S. Cl.
CPC ........ *A61N 1/36128* (2013.01); *A61N 1/36142* (2013.01); *A61N 1/3718* (2013.01);
(Continued)

(58) Field of Classification Search
CPC ........... A61N 1/36128; A61N 1/36142; A61N 1/36521; A61N 1/3718; A61N 1/3925
USPC .............................................. 607/59, 62, 63
See application file for complete search history.

(56) References Cited

U.S. PATENT DOCUMENTS

| 6,516,227 B1 | 2/2003 | Meadows et al. |
| 6,895,280 B2 | 5/2005 | Meadows et al. |

(Continued)

FOREIGN PATENT DOCUMENTS

EP          0038080          10/1981

OTHER PUBLICATIONS

U.S. Appl. No. 61/612,241, Neurostimulation System for Preventing Magnetically Induced Currents in Electronic Circuitry, Inventor: Kiran Gururaj, et al., filing date: Mar. 16, 2012.

(Continued)

*Primary Examiner* — Christopher D Koharski
*Assistant Examiner* — Michael Carey
(74) *Attorney, Agent, or Firm* — Lowe Graham Jones PLLC; Bruce E. Black (57) ABSTRACT

An implantable medical device capable of being placed between a first operational mode and a second operational mode. The medical device comprises a magnetic field sensing device for outputting a signal in response to sensing a magnetic field. The medical device further comprises a logic circuit for continuously asserting the signal during a time period when the neurostimulation device is in the first operational mode, and intermittently asserting the signal during at least one time period when the neurostimulation device is in the second operational mode. The medical device further comprises a delay circuit for introducing a time delay into the asserted signal, the time delay being less than the time period, but greater than each of the at least one time period. The medical device further comprises control circuitry for performing a function in response to receiving the delayed signal at a first input terminal.

19 Claims, 10 Drawing Sheets

(51) Int. Cl.
*A61N 1/39* (2006.01)
*A61N 1/37* (2006.01)
*A61N 1/362* (2006.01)

(52) U.S. Cl.
CPC .............. *A61N1/3925* (2013.01); *A61N 1/362* (2013.01); *A61N 1/36003* (2013.01); *A61N 1/3605* (2013.01); *A61N 1/36007* (2013.01); *A61N 1/36082* (2013.01); *A61N 1/3956* (2013.01)

(56) References Cited

U.S. PATENT DOCUMENTS

| | | |
|---|---|---|
| 7,539,538 B2 | 5/2009 | Parramon et al. |
| 7,650,184 B2 | 1/2010 | Walter |
| 8,019,439 B2 | 9/2011 | Kuzma et al. |
| 2003/0139781 A1 | 7/2003 | Bradley et al. |
| 2005/0267546 A1 | 12/2005 | Parramon et al. |
| 2007/0150036 A1 | 6/2007 | Anderson |
| 2007/0168004 A1 | 7/2007 | Walter |
| 2007/0168007 A1 | 7/2007 | Kuzma et al. |
| 2007/0173890 A1 | 7/2007 | Armstrong |
| 2009/0157146 A1* | 6/2009 | Linder et al. .................. 607/60 |
| 2011/0238135 A1 | 9/2011 | Marnfeldt et al. |

OTHER PUBLICATIONS

PCT International Search Report for PCT/US2013/047684, Applicant: Boston Scientific Neuromodulation Corporation, Form PCT/ISA/210 and 220, dated Oct. 4, 2013 (4pages).

PCT Written Opinion of the International Search Authority for PCT/US2013/047684, Applicant: Boston Scientific Neuromodulation Corporation, Form PCT/ISA/237, dated Oct. 4, 2013 (7pages).

* cited by examiner

NEUROSTIMULATION SYSTEM FOR ENABLING MAGNETIC FIELD SENSING WITH A SHUT-DOWN HALL SENSOR

RELATED APPLICATION DATA

The present application claims the benefit under 35 U.S.C. §119 to U.S. provisional patent application Ser. No. 61/664,061, filed Jun. 25, 2012. The foregoing application is hereby incorporated by reference into the present application in its entirety.

FIELD OF THE INVENTION

The present invention relates to tissue stimulation systems, and in particular, MRI-compatible neurostimulators.

BACKGROUND OF THE INVENTION

Implantable neurostimulation systems have proven therapeutic in a wide variety of diseases and disorders. Pacemakers and Implantable Cardiac Defibrillators (ICDs) have proven highly effective in the treatment of a number of cardiac conditions (e.g., arrhythmias). Spinal Cord Stimulation (SCS) systems have long been accepted as a therapeutic modality for the treatment of chronic pain syndromes, and the application of tissue stimulation has begun to expand to additional applications such as angina pectoralis and incontinence. Deep Brain Stimulation (DBS) has also been applied therapeutically for well over a decade for the treatment of refractory chronic pain syndromes, and DBS has also recently been applied in additional areas such as movement disorders and epilepsy. Further, in recent investigations Peripheral Nerve Stimulation (PNS) systems have demonstrated efficacy in the treatment of chronic pain syndromes and incontinence, and a number of additional applications are currently under investigation. Furthermore, Functional Electrical Stimulation (FES) systems such as the Freehand system by NeuroControl (Cleveland, Ohio) have been applied to restore some functionality to paralyzed extremities in spinal cord injury patients.

Each of these implantable neurostimulation systems typically includes at least one stimulation lead implanted at the desired stimulation site and an Implantable Pulse Generator (IPG) implanted remotely from the stimulation site, but coupled either directly to the stimulation lead(s) or indirectly to the stimulation lead(s) via one or more lead extensions. Thus, electrical pulses can be delivered from the neurostimulator to the electrodes carried by the stimulation lead(s) to stimulate or activate a volume of tissue in accordance with a set of stimulation parameters and provide the desired efficacious therapy to the patient. The neurostimulation system may further comprise a handheld Remote Control (RC) to remotely instruct the neurostimulator to generate electrical stimulation pulses in accordance with selected stimulation parameters. The RC may, itself, be programmed by a technician attending the patient, for example, by using a Clinician's Programmer (CP), which typically includes a general purpose computer, such as a laptop, with a programming software package installed thereon.

Significant to the present inventions described herein, a typical IPG may be manually inactivated by the patient, e.g., to cease stimulation of the IPG during an emergency, by placing a magnet over the implanted IPG. This can be accomplished using any one of several different types of magnetically induced shut-down circuits.

Figure 1:
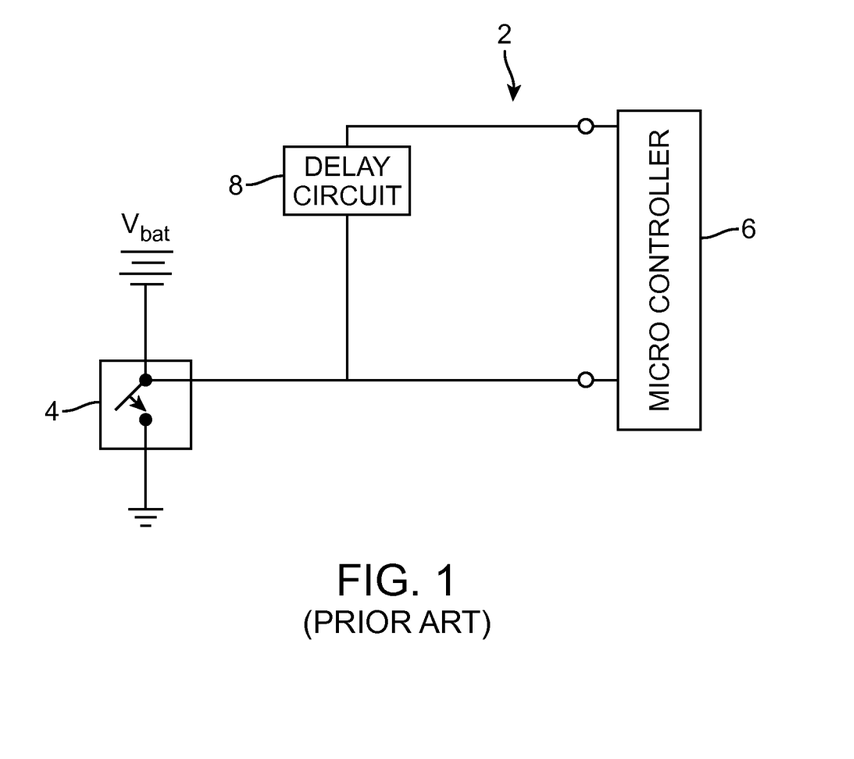
FIG. 1 is a prior art embodiment of magnetically induced shut-down circuitry used in an implantable pulse generator (IPG)

For example, referring to FIG. 1, one implementation of magnetically induced shut-down circuitry 2 generally comprises a magnetic field sensing device 4, such as a reed switch or a Hall sensor, a microcontroller 6, which controls and manages the operations of the IPG, and a delay circuit 8, which introduces a delay into an input of, e.g., 200-400 μs. The output of the magnetic field sensing device 4 is coupled to an interrupt pin of the microcontroller 6, and further coupled to a reset pin of the microcontroller 6 via the delay circuit 8. Thus, when the magnetic field sensing device 4 senses a magnetic field, such as that emitted by a magnet passed over the IPG, a switch within the magnetic field sensing device 4 closes, thereby outputting a signal indicating the desire of the patient or user to cease stimulation. The signal is conveyed to the interrupt pin of the microcontroller 6, which responds by instantaneously shutting down power to the stimulation circuitry (now shown) of the IPG, thereby ceasing stimulation of the patient, as well as performing housekeeping functions, such as storing data. The signal is also conveyed to the reset pin of the microcontroller 6, which responds by rebooting itself. Significantly, the delay introduced by the delay circuit 8 into the signal output by the magnetic field sensing device 4 allows the microcontroller 6 to perform the aforementioned housekeeping functions prior to rebooting.

IPGs are routinely implanted in patients who are in need of Magnetic Resonance Imaging (MRI). Thus, when designing implantable neurostimulation systems, consideration must be given to the possibility that the patient in which neurostimulator is implanted may be subjected to electro-magnetic forces generated by MRI scanners, which may potentially cause damage to the neurostimulator as well as discomfort to the patient.

In particular, in MRI, spatial encoding relies on successively applying magnetic field gradients. The magnetic field strength is a function of position and time with the application of gradient fields throughout the imaging process. Gradient fields typically switch gradient coils (or magnets) ON and OFF thousands of times in the acquisition of a single image in the present of a large static magnetic field. Present-day MRI scanners can have maximum gradient strengths of 100 mT/m and much faster switching times (slew rates) of 150 mT/m/ms, which is comparable to stimulation therapy frequencies. Typical MRI scanners create gradient fields in the range of 100 Hz to 30 KHz, and radio frequency (RF) fields of 64 MHz for a 1.5 Tesla scanner and 128 MHz for a 3 Tesla scanner.

Despite the fact that a conventional IPG implanted within a patient undergoing an MRI will be automatically deactivated (i.e., the magnetic field present in the MRI scanner will be sensed by the magnetic field sensing device, thereby automatically deactivating the IPG), the strength of the gradient magnetic field may be high enough to induce voltages (5-10 Volts depending on the orientation of the lead inside the body with respect to the MRI scanner) on to the stimulation lead(s), which in turn, are seen by the IPG electronics. If these induced voltages are higher than the voltage supply rails of the IPG electronics, there could exist paths within the IPG that could induce current through the electrodes on the stimulation lead(s), which in turn, could cause unwanted stimulation to the patient due to the similar frequency band, between the MRI-generated gradient field and intended stimulation energy frequencies for therapy, as well as potentially damaging the electronics within the IPG. To elaborate further, the gradient (magnetic) field may induce electrical energy within the wires of the stimulation lead(s), which may be conveyed into the circuitry of the IPG and then out to the electrodes of the stimulation leads. For example, in a conventional neurostimulation system, an induced voltage at the connector of the IPG that is higher than IPG battery voltage (~4-5V), may induce such unwanted stimulation currents. RF energy generated by the MRI scanner may induce electrical currents of even higher voltages within the IPG.

In one novel technique described in U.S. Provisional Patent Application Ser. No. 61/612,214, entitled "Neurostimulation System for Preventing Magnetically Induced Currents in Electronic Circuitry," which is expressly incorporated herein by reference, voltage supply rails of the IPG electronics are increased in response to an external signal from the RC or CP that places the IPG in an MRI-mode. In order to increase the voltage supply rails of the IPG electronics, it is necessary that the IPG not be deactivated in the presence of the magnetic field generated by the MRI scanner. In one proposed method, this can be accomplished by disabling the magnetic field sensing device to prevent deactivation of the IPG. However, it may be desirable to continue to monitor the magnetic field generated by the MRI, e.g., to determine when the MRI has been initiated and/or terminated. If the magnetic field sensing device is disabled during the MRI, this function cannot be accomplished.

There, thus, remains a need to prevent an IPG from being deactivated during an MRI, while monitoring the magnetic field during the MRI.

SUMMARY OF THE INVENTION

In accordance with a first aspect of the present inventions, an implantable medical device capable of being placed between a first operational mode (e.g., a normal mode) and a second operational mode (an MRI-mode) is provided. The implantable medical device comprises a magnetic field sensing device (e.g., a reed switch or a Hall sensor) configured for outputting a signal in response to sensing a magnetic field.

The medical device further comprises a logic circuit configured for continuously asserting the signal when the neurostimulation device is in the first operational mode, and intermittently asserting the signal during at least one time period when the neurostimulation device is in the second operational mode. In one embodiment, the signal is intermittently asserted during a plurality of successive time periods, e.g., in accordance with a duty cycle. The medical device further comprises a delay circuit coupled between the magnetic field sensing device and the first input terminal of the control circuitry, the delay circuit configured for introducing a time delay (e.g., in the range of 200 ms-400 ms) into the signal. The time delay is less than the time period during which the signal is continuously asserted, but greater than each of the time period(s) during which the signal is intermittently asserted. In one embodiment, the logic circuit comprises a logic gate (e.g., an AND-gate or a NOR-gate) and a register configured for storing a signal assertion bit, with the logic gate having a first input coupled to the magnetic field sensing device, and a second input coupled to the register.

The medical device further comprises control circuitry configured for performing a function (e.g., deactivating the medical device) in response to receiving the delayed signal at a first input terminal. The control circuitry may be configured for performing another function (e.g., recording information based on the sensed magnetic field) in response to receiving the signal at a second input terminal. An optional embodiment of the medical device comprises a plurality of electrical terminals configured for being respectively coupled to a plurality of stimulation electrodes, and stimulation output circuitry configured for outputting electrical stimulation energy to the plurality of electrical terminals.

In accordance with a second aspect of the present inventions, a method of operating a medical device implanted within a patient is provided.

The method comprises, when the medical device is in a first operational mode (e.g., when the patient is not undergoing an MRI), generating a first signal in response to sensing a magnetic field, continuously asserting the first signal, introducing a time delay into the first asserted signal, wherein the time delay is less than the time period, thereby prompting the neurostimulation device to perform a function (e.g., deactivating the medical device) in response to the first delayed signal.

The method further comprises, when the medical device is in a second operational mode (when the patient is undergoing an MRI), generating a second signal in response to sensing a magnetic field, intermittently asserting the second signal during at least one time period, introducing a time delay into the second asserted signal, wherein the time delay (e.g., in the range of 200 ms-400 ms) is greater than each of the at least one time period, thereby preventing the neurostimulation device from performing the function in response to the second delayed signal. The second signal may be intermittently asserted during a plurality of successive time periods, e.g., in accordance with a duty cycle. The method may optionally further comprise performing another function (e.g., recording information based on the sensed magnetic field) in response to the second asserted signal when the medical device is in the second operational mode.

Other and further aspects and features of the invention will be evident from reading the following detailed description of the preferred embodiments, which are intended to illustrate, not limit, the invention.

BRIEF DESCRIPTION OF THE DRAWINGS

The drawings illustrate the design and utility of preferred embodiments of the present invention, in which similar elements are referred to by common reference numerals. In order to better appreciate how the above-recited and other advantages and objects of the present inventions are obtained, a more particular description of the present inventions briefly described above will be rendered by reference to specific embodiments thereof, which are illustrated in the accompanying drawings. Understanding that these drawings depict only typical embodiments of the invention and are not therefore to be considered limiting of its scope, the invention will be described and explained with additional specificity and detail through the use of the accompanying drawings in which.

DETAILED DESCRIPTION OF THE EMBODIMENTS

The description that follows relates to a spinal cord stimulation (SCS) system. However, it is to be understood that the while the invention lends itself well to applications in SCS, the invention, in its broadest aspects, may not be so limited. Rather, the invention may be used with any type of implantable electrical circuitry used to stimulate tissue. For example, the present invention may be used as part of a pacemaker, a defibrillator, a cochlear stimulator, a retinal stimulator, a stimulator configured to produce coordinated limb movement, a cortical stimulator, a deep brain stimulator, peripheral nerve stimulator, microstimulator, or in any other neural stimulator configured to treat urinary incontinence, sleep apnea, shoulder sublaxation, headache, etc.

Figure 2:
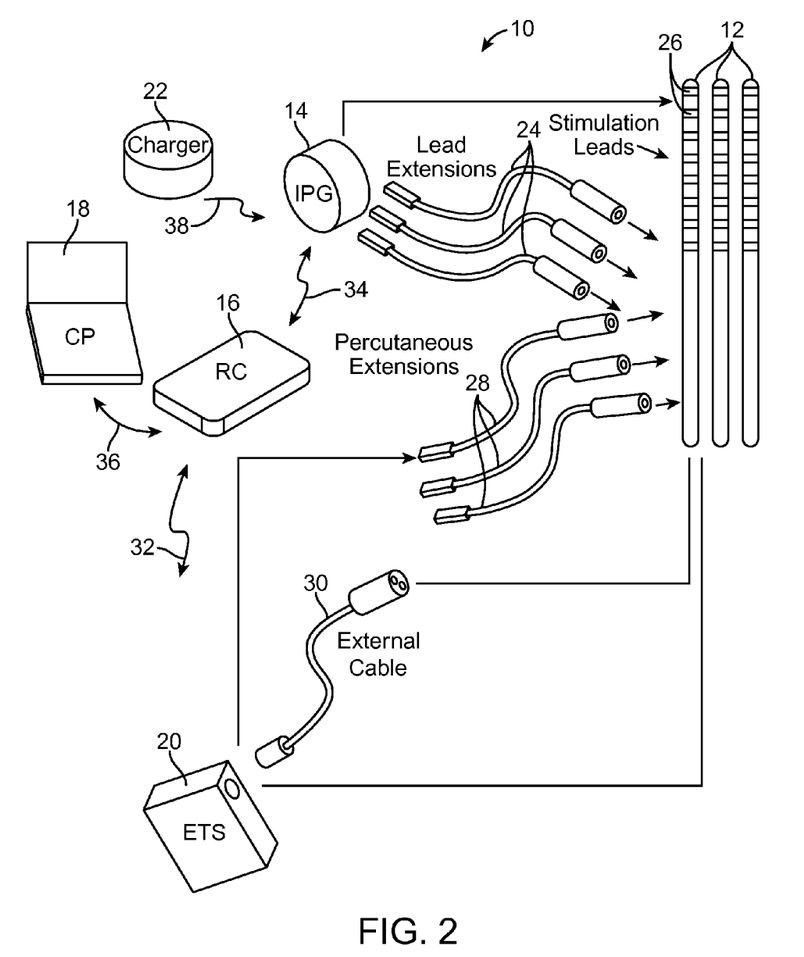
FIG. 2 is a plan view of a Spinal Cord Stimulation (SCS) system constructed in accordance with one embodiment of the present inventions.

Turning first to FIG. 2, an exemplary spinal cord stimulation (SCS) system 10 generally includes one or more (in this case, three) implantable stimulation leads 12, a pulse generating device in the form of an implantable pulse generator (IPG) 14, an external control device in the form of a remote controller RC 16, a clinician's programmer (CP) 18, an external trial stimulator (ETS) 20, and an external charger 22.

The IPG 14 is physically connected via one or more lead extensions 24 to the stimulation leads 12, which carry a plurality of electrodes 26 arranged in an array. The stimulation leads 12 are illustrated as percutaneous leads in FIG. 2, although as will be described in further detail below, a surgical paddle lead can be used in place of the percutaneous leads. As will also be described in further detail below, the IPG 14 includes pulse generation circuitry that delivers electrical stimulation energy in the form of a pulsed electrical waveform (i.e., a temporal series of electrical pulses) to the electrode array 26 in accordance with a set of stimulation parameters.

The ETS 20 may also be physically connected via the percutaneous lead extensions 28 and external cable 30 to the stimulation leads 12. The ETS 20, which has similar pulse generation circuitry as the IPG 14, also delivers electrical stimulation energy in the form of a pulse electrical waveform to the electrode array 26 accordance with a set of stimulation parameters. The major difference between the ETS 20 and the IPG 14 is that the ETS 20 is a non-implantable device that is used on a trial basis after the stimulation leads 12 have been implanted and prior to implantation of the IPG 14, to test the responsiveness of the stimulation that is to be provided. Thus, any functions described herein with respect to the IPG 14 can likewise be performed with respect to the ETS 20.

The RC 16 may be used to telemetrically control the ETS 20 via a bi-directional RF communications link 32. Once the IPG 14 and stimulation leads 12 are implanted, the RC 16 may be used to telemetrically control the IPG 14 via a bi-directional RF communications link 34. Such control allows the IPG 14 to be turned on or off and to be programmed with different stimulation parameter sets. The IPG 14 may also be operated to modify the programmed stimulation parameters to actively control the characteristics of the electrical stimulation energy output by the IPG 14. As will be described in further detail below, the CP 18 provides clinician detailed stimulation parameters for programming the IPG 14 and ETS 20 in the operating room and in follow-up sessions.

The CP 18 may perform this function by indirectly communicating with the IPG 14 or ETS 20, through the RC 16, via an IR communications link 36. Alternatively, the CP 18 may directly communicate with the IPG 14 or ETS 20 via an RF communications link (not shown). The clinician detailed stimulation parameters provided by the CP 18 are also used to program the RC 16, so that the stimulation parameters can be subsequently modified by operation of the RC 16 in a stand-alone mode (i.e., without the assistance of the CP 18).

For purposes of brevity, the details of the RC 16, CP 18, ETS 20, and external charger 22 will not be described herein. Details of exemplary embodiments of these devices are disclosed in U.S. Pat. No. 6,895,280, which is expressly incorporated herein by reference.

Figure 3:
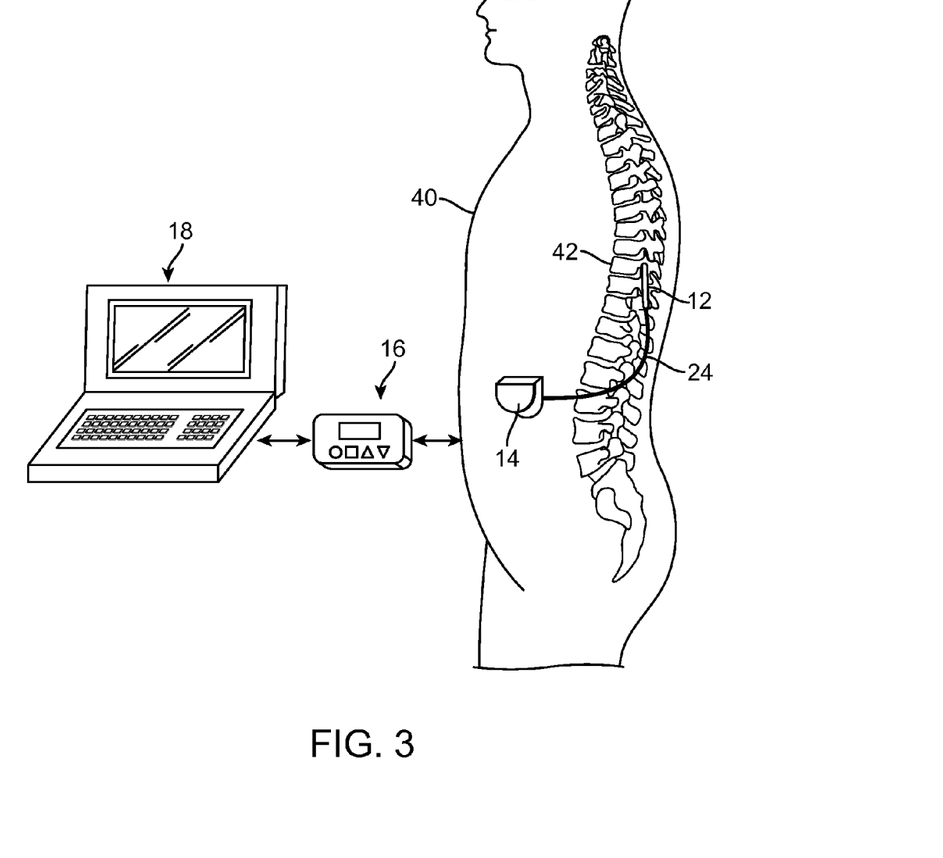
FIG. 3 is a plan view of the SCS system of FIG. 2 in use within a patient.

As shown in FIG. 3, the stimulation leads 12 are implanted within the spinal column 42 of a patient 40. The preferred placement of the electrode leads 12 is adjacent, i.e., resting near, the spinal cord area to be stimulated. Due to the lack of space near the location where the electrode leads 12 exit the spinal column 42, the IPG 14 is generally implanted in a surgically-made pocket either in the abdomen or above the buttocks. The IPG 14 may, of course, also be implanted in other locations of the patient's body. The lead extensions 24 facilitate locating the IPG 14 away from the exit point of the electrode leads 12. As there shown, the CP 18 communicates with the IPG 14 via the RC 16.

Figure 4:
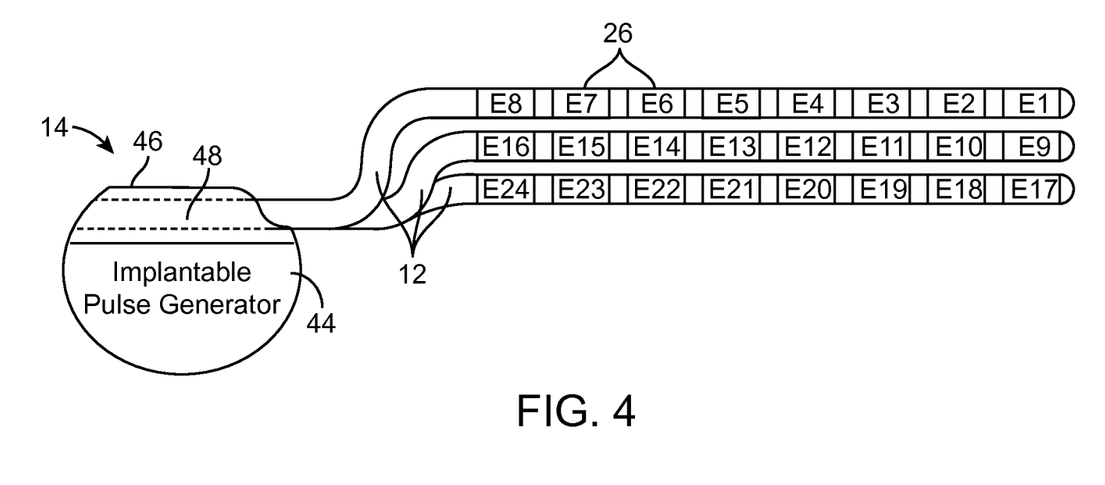
FIG. 4 is a plan view of an implantable pulse generator (IPG) and three percutaneous stimulation leads used in the SCS system of FIG. 2.

Referring now to FIG. 4, the external features of the stimulation leads 12 and the IPG 14 will be briefly described. Each of the stimulation leads 12 has eight electrodes 26 (respectively labeled E1-E8, E9-E16, and E17-E24). The actual number and shape of leads and electrodes will, of course, vary according to the intended application. Further details describing the construction and method of manufacturing percutaneous stimulation leads are disclosed in U.S. patent application Ser. No. 11/689,918, entitled "Lead Assembly and Method of Making Same," and U.S. patent application Ser. No. 11/565,547, entitled "Cylindrical Multi-Contact Electrode Lead for Neural Stimulation and Method of Making Same," the disclosures of which are expressly incorporated herein by reference.

Figure 5:
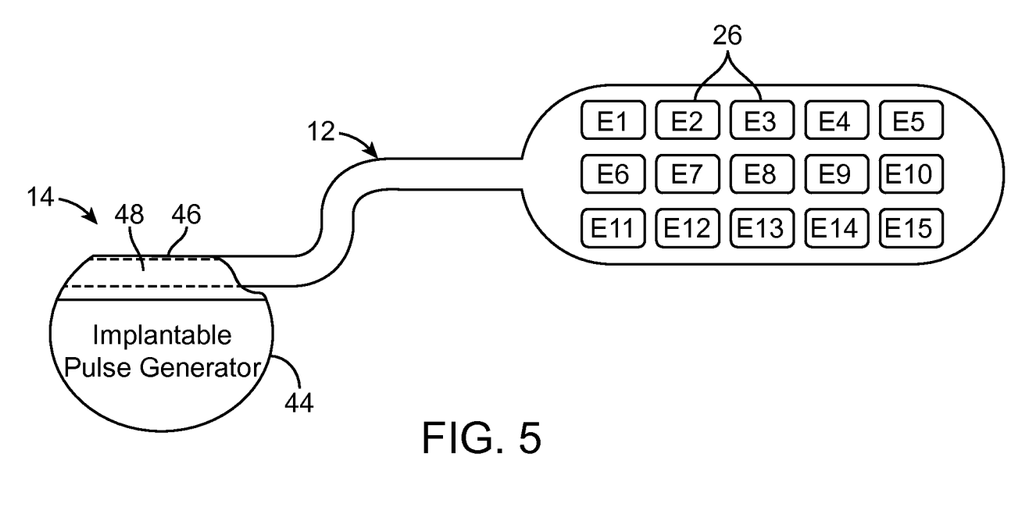
FIG. 5 is a plan view of an implantable pulse generator (IPG) and a surgical paddle lead used in the SCS system of FIG. 2.

Alternatively, as illustrated in FIG. 5, the stimulation lead 12 takes the form of a surgical paddle lead on which electrodes 26 are arranged in a two-dimensional array in three columns (respectively labeled E1-E5, E6-E10, and E11-E15) along the axis of the stimulation lead 12. In the illustrated embodiment, five rows of electrodes 26 are provided, although any number of rows of electrodes can be used. Each row of the electrodes 26 is arranged in a line transversely to the axis of the lead 12. The actual number of leads and electrodes will, of course, vary according to the intended application. Further details regarding the construction and method of manufacture of surgical paddle leads are disclosed in U.S. patent application Ser. No. 11/319,291, entitled "Stimulator Leads and Methods for Lead Fabrication," the disclosure of which is expressly incorporated herein by reference.

In each of the embodiments illustrated in FIGS. 4 and 5, the IPG 14 comprises an outer case 44 for housing the electronic and other components (described in further detail below). The outer case 44 is composed of an electrically conductive, biocompatible material, such as titanium, and forms a hermetically sealed compartment wherein the internal electronics are protected from the body tissue and fluids. In some cases, the outer case 44 may serve as an electrode. The IPG 14 further comprises a connector 46 to which the proximal ends of the stimulation leads 12 mate in a manner that electrically couples the electrodes 26 to the internal electronics (described in further detail below) within the outer case 44. To this end, the connector 46 includes one or more ports (three ports 48 or three percutaneous leads or one port for the surgical paddle lead) for receiving the proximal end(s) of the stimulation lead(s) 12. In the case where the lead extensions 24 are used, the port(s) 48 may instead receive the proximal ends of such lead extensions 24.

The IPG 14 includes pulse generation circuitry that provides electrical conditioning and stimulation energy in the form of a pulsed electrical waveform to the electrode array 26 in accordance with a set of stimulation parameters programmed into the IPG 14. Such stimulation parameters may comprise electrode combinations, which define the electrodes that are activated as anodes (positive), cathodes (negative), and turned off (zero), percentage of stimulation energy assigned to each electrode (fractionalized electrode configurations), and electrical pulse parameters, which define the pulse amplitude (measured in milliamps or volts depending on whether the IPG 14 supplies constant current or constant voltage to the electrode array 26), pulse width (measured in microseconds), pulse rate (measured in pulses per second), and burst rate (measured as the stimulation on duration X and stimulation off duration Y).

Electrical stimulation will occur between two (or more) activated electrodes, one of which may be the IPG case 44. Simulation energy may be transmitted to the tissue in a monopolar or multipolar (e.g., bipolar, tripolar, etc.) fashion. Monopolar stimulation occurs when a selected one of the lead electrodes 26 is activated along with the case 44 of the IPG 14, so that stimulation energy is transmitted between the selected electrode 26 and the case 44. Bipolar stimulation occurs when two of the lead electrodes 26 are activated as anode and cathode, so that stimulation energy is transmitted between the selected electrodes 26. For example, an electrode on one lead 12 may be activated as an anode at the same time that an electrode on the same lead or another lead 12 is activated as a cathode. Tripolar stimulation occurs when three of 15 the lead electrodes 26 are activated, two as anodes and the remaining one as a cathode, or two as cathodes and the remaining one as an anode. For example, two electrodes on one lead 12 may be activated as anodes at the same time that an electrode on another lead 12 is activated as a cathode.

The stimulation energy may be delivered between electrodes as monophasic electrical energy or multiphasic electrical energy. Monophasic electrical energy includes a series of pulses that are either all positive (anodic) or all negative (cathodic). Multiphasic electrical energy includes a series of pulses that alternate between positive and negative. For example, multiphasic electrical energy may include a series of biphasic pulses, with each biphasic pulse including a cathodic (negative) stimulation pulse and an anodic (positive) recharge pulse that is generated after the stimulation pulse to prevent direct current charge transfer through the tissue, thereby avoiding electrode degradation and cell trauma. That is, charge is conveyed through the electrode-tissue interface via current at an electrode during a stimulation period (the length of the stimulation pulse), and then pulled back off the electrode-tissue interface via an oppositely polarized current at the same electrode during a recharge period (the length of the recharge pulse).

Figure 6:
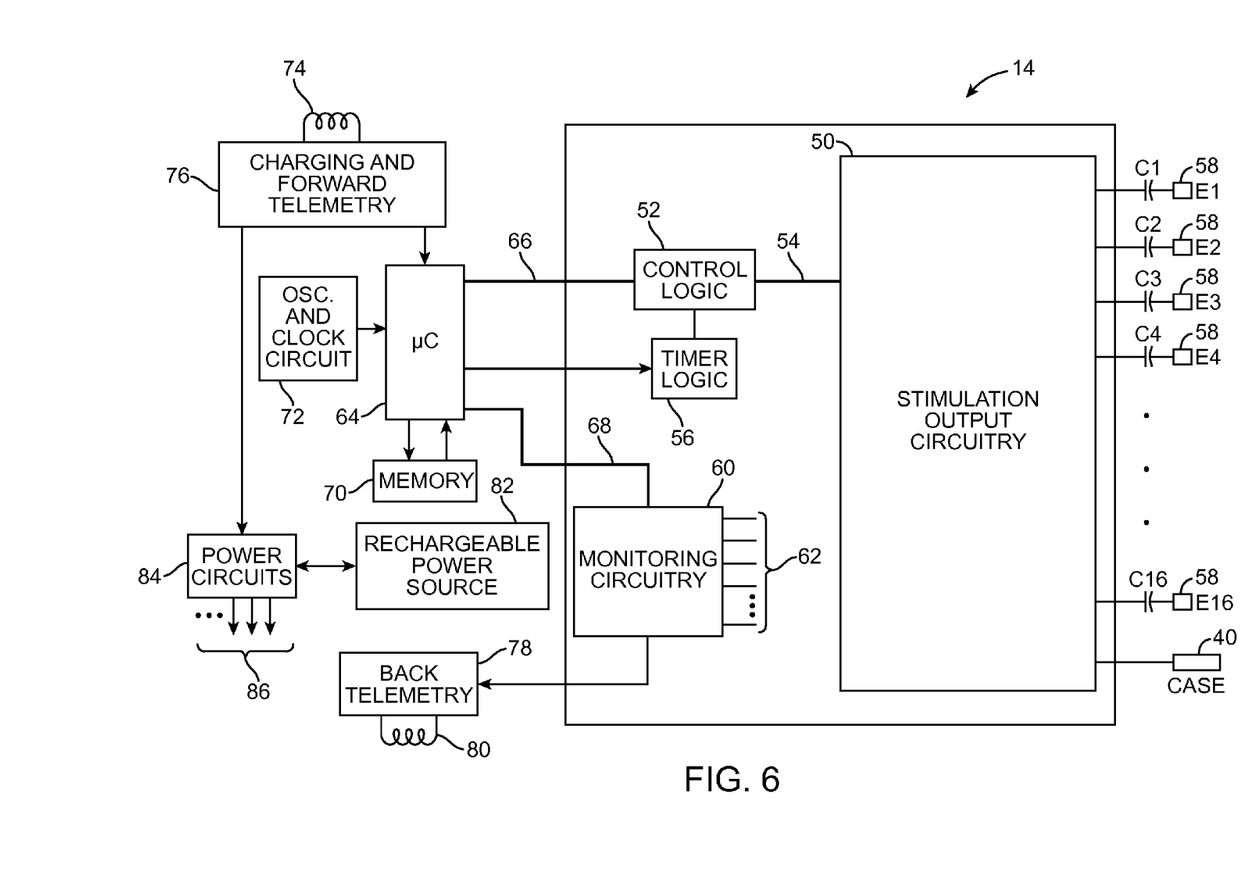
FIG. 6 is a block diagram of the internal components of the IPG of FIGS. 4 and 5.

Turning next to FIG. 6, the main internal components of the IPG 14 will now be described. The IPG 14 includes stimulation output circuitry 50 configured for generating electrical stimulation energy in accordance with a defined pulsed waveform having a specified pulse amplitude, pulse rate, pulse width, pulse shape, and burst rate under control of control logic 52 over data bus 54. Control of the pulse rate and pulse width of the electrical waveform is facilitated by timer logic circuitry 56, which may have a suitable resolution, e.g., 10 μs. The stimulation energy generated by the stimulation output circuitry 50 is output via capacitors C1-Cn to electrical terminals 58 corresponding to the electrodes 26. In the illustrated embodiment, the stimulation output circuitry 50 may either comprise independently controlled current sources for providing stimulation pulses of a specified and known amperage to or from the electrodes 26, or independently controlled voltage sources for providing stimulation pulses of a specified and known voltage at the electrodes 26. The stimulation output circuitry 50 further includes charge recovery circuitry (not shown) to provide charge balancing of the electrodes and recovery of charge from the tissue.

The IPG 14 further comprises monitoring circuitry 60 for monitoring the status of various nodes or other points 62 throughout the IPG 14, e.g., power supply voltages, temperature, battery voltage, and the like. The monitoring circuitry 60 is also configured for measuring electrical parameter data (e.g., electrode impedance and/or electrode field potential). As will be described in further detail below, the monitoring circuitry 60 is also configured for sensing a magnetic field. The IPG 14 further comprises processing circuitry in the form of a microcontroller (μC) 64 that controls the control logic 52 over data bus 66, and obtains status data from the monitoring circuitry 60 via data bus 68. The IPG 14 additionally controls the timer logic 56. The IPG 14 further comprises memory 70 and oscillator and clock circuit 72 coupled to the microcontroller 64. The microcontroller 64, in combination with the memory 70 and oscillator and clock circuit 72, thus comprise a microprocessor system that carries out a program function in accordance with a suitable program stored in the memory 70. Alternatively, for some applications, the function provided by the microprocessor system may be carried out by a suitable state machine.

Thus, the microcontroller 64 generates the necessary control and status signals, which allow the microcontroller 64 to control the operation of the IPG 14 in accordance with a selected operating program and stimulation parameters. In controlling the operation of the IPG 14, the microcontroller 64 is able to individually generate stimulus pulses at the electrodes 26 using the stimulation output circuitry 50, in combination with the control logic 52 and timer logic 56, thereby allowing each electrode 26 to be paired or grouped with other electrodes 26, including the monopolar case electrode, to control the polarity, amplitude, rate, pulse width and channel through which the current stimulus pulses are provided.

Significantly, in response to an external signal, the microcontroller 64 places the IPG 14 in either a normal mode, during which the IPG 14 will shut the IPG 14 down when a conventional magnetic is passed over the skin of the patient above the IPG 14, and an MRI-mode, during which the microcontroller 64 will not shut the IPG 14 down, but rather will monitor the sensed magnetic energy, when an MRI is performed on the patient. To this end, the monitoring circuitry 60 comprises a magnetic field sensing assembly 100 (shown in FIG. 7) configured for outputting a signal, which is continuously asserted when the IPG 14 is in the normal mode in order to prompt the microcontroller 64 to shut the IPG 14 down, and is alternately asserted and de-asserted when the IPG 14 is in the MRI-mode in order to allow the microcontroller 64 to sense the magnetic field without shutting the IPG 14 down, as will be described in further detail below.

The IPG 14 further comprises an alternating current (AC) receiving coil 74 for receiving programming data (e.g., the operating program, and/or stimulation parameters, and/or a signal for placing the IPG 14 in either the normal mode or the MRI-mode) from the RC 16 and/or CP 18 in an appropriate modulated carrier signal, and charging and forward telemetry circuitry 76 for demodulating the carrier signal it receives through the AC receiving coil 74 to recover the programming data, which programming data is then stored within the memory 70, or within other memory elements (not shown) distributed throughout the IPG 14.

The IPG 14 further comprises back telemetry circuitry 78 and an alternating current (AC) transmission coil 80 for sending informational data sensed through the monitoring circuitry 60 to the RC 16 and/or CP 18. The back telemetry features of the IPG 14 also allow its status to be checked. For example, when the RC 16 and/or CP 18 initiates a programming session with the IPG 14, the capacity of the battery is telemetered, so that the RC 16 and/or CP 18 can calculate the estimated time to recharge. Any changes made to the current stimulus parameters are confirmed through back telemetry, thereby assuring that such changes have been correctly received and implemented within the implant system. Moreover, upon interrogation by the RC 16 and/or CP 18, all programmable settings stored within the IPG 14 may be uploaded to the RC 16 and/or CP 18.

The IPG 14 further comprises a rechargeable power source 82 and power circuits 84 for providing the operating power to the IPG 14. The rechargeable power source 82 may, e.g., comprise a lithium-ion or lithium-ion polymer battery. The rechargeable battery 82 provides an unregulated voltage to the power circuits 84 (e.g., 3V). The power circuits 84, in turn, generate the various voltages 86, some of which are regulated and some of which are not, as needed by the various circuits located within the IPG 14. As will be described in further detail below, the power circuits 84 include a high voltage generation (HVG) circuit that converts the battery voltage to a higher voltage under control of the microcontroller 64 in order to prevent electrical current induced by strong magnetic fields, such as those generated by magnetic resonance image (MRI) scanners, from creating a loop within the charge recovery circuit that could cause inadvertent stimulation of the patient.

The rechargeable power source 82 is recharged using rectified AC power (or DC power converted from AC power through other means, e.g., efficient AC-to-DC converter circuits, also known as "inverter circuits") received by the AC receiving coil 74. To recharge the power source 82, the external charger 22 (shown in FIG. 2), which generates the AC magnetic field, is placed against, or otherwise adjacent, to the patient's skin over the implanted IPG 14. The AC magnetic field emitted by the external charger induces AC currents in the AC receiving coil 74. The charging and forward telemetry circuitry 76 rectifies the AC current to produce DC current, which is used to charge the power source 82. While the AC receiving coil 74 is described as being used for both wirelessly receiving communications (e.g., programming and control data) and charging energy from the external device, it should be appreciated that the AC receiving coil 74 can be arranged as a dedicated charging coil, while another coil, such as coil 80, can be used for bi-directional telemetry.

Additional details concerning the above-described and other IPGs may be found in U.S. Pat. No. 6,516,227, U.S. Patent Publication No. 2003/0139781, and U.S. patent application Ser. No. 11/138,632, entitled "Low Power Loss Current Digital-to-Analog Converter Used in an Implantable Pulse Generator," which are expressly incorporated herein by reference. It should be noted that rather than an IPG, the system 10 may alternatively utilize an implantable receiver-stimulator (not shown) connected to leads 12. In this case, the power source, e.g., a battery, for powering the implanted receiver, as well as control circuitry to command the receiver-stimulator, will be contained in an external controller inductively coupled to the receiver-stimulator via an electromagnetic link. Data/power signals are transcutaneously coupled from a cable-connected transmission coil placed over the implanted receiver-stimulator. The implanted receiver-stimulator receives the signal and generates the stimulation in accordance with the control signals.

Figure 7:
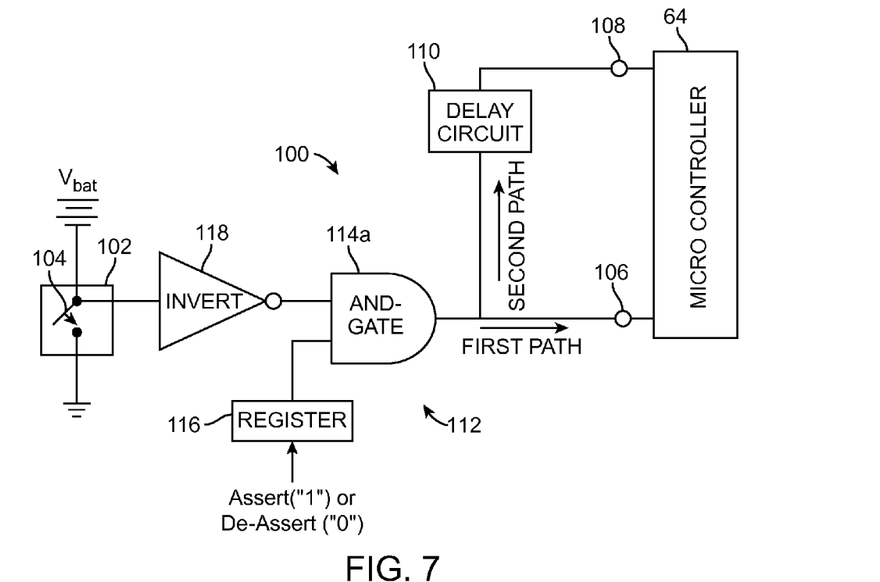
FIG. 7 is a block diagram illustrating the components of one embodiment of a magnetic field sensing assembly used in the IPG of FIGS. 4 and 5.

Referring now to FIG. 7, the magnetic field sensing assembly 100 comprises a magnetic field sensing device 102 (e.g., a reed switch or a Hall sensor) configured for outputting a signal in response to sensing a magnetic field. In the illustrated embodiment, the magnetic field sensing device 102 includes a switch 104 coupled between the battery 82 and ground. Thus, when the magnetic field sensing device 102 senses the magnetic field, the switch 104 is closed, thereby creating a logical "0" at the output of the magnetic field sensing device 102, and when the magnetic field sensing device 102 does not sense the magnetic field, the switch 104 is open, thereby creating a logical "1" at the output of the magnetic field sensing device 102. Alternatively, the switch 104 can be closed when no magnetic field is sensed, and opened when the magnetic field is sensed. In any event, the status of the signal at the output of the magnetic field sensing device 102 changes between the sensing of a magnetic field and the sensing of no magnetic field.

This signal, when asserted, is conveyed to one or more input terminals of the microcontroller 64. In particular, the asserted signal may be conveyed along two separate paths to input terminals 106, 108 of the microcontroller 64. In response to the arrival of the signal on the input terminal 106, the microcontroller 64 instructs the stimulation output circuitry 50 to cease generating electrical stimulation energy to the extent that it was previously doing so, and records information, such as the current time and/or temperature. In response to the arrival of the signal on the input terminal 108, the microcontroller 64 deactivates the IPG 14 by shutting down power to the IPG circuitry. In order to allow the microcontroller 64 to perform housekeeping functions, the magnetic field sensing assembly 100 comprises a delay circuit 110 coupled between the magnetic field sensing device 102 and the microcontroller 64 along the second path. In the illustrated embodiment, the delay circuit 110 introduces a delay into the signal in the range of 200 ms-400 ms.

The signal that prompts the microcontroller 64 to perform the afore-mentioned functions can either be a logical "1" or a logical "0," depending upon the desire of the designer. The nature of the signal that arrives at the input terminals 106, 108 of the microcontroller 64 may differ from the nature of the signal output by the magnetic field sensing device 102. For example, a logic inverter may be placed within the paths between the magnetic field sensing device 102 and the microcontroller 64, such that the signal may be a logical "0" at the output of the magnetic field sensing device 102, but may be a logical "1" at any of the input terminals 106, 108 of the microcontroller 64. In any event, the magnetic field sensing device 102 generates a signal that the microcontroller 64 can interpret as a magnetic field sensing event.

Figure 9:
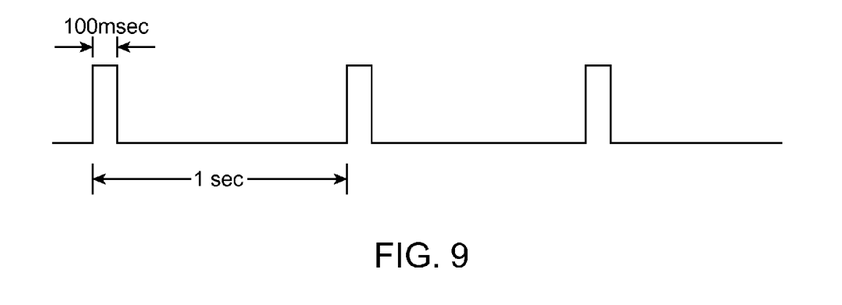
FIG. 9 is a timing diagram of a signal assertion/de-assertion waveform used by a logic circuit in the magnetic field sensing assembly of FIG. 8.

The magnetic field sensing assembly 100 further comprises a logic circuit 112 configured for continuously asserting the signal during a time period when the IPG 14 is in the normal mode, and intermittently asserting the signal during at least one time period when the IPG 14 is in the MRI-mode. In the illustrated embodiment, when the IPG 14 is in the MRI-mode, the logic circuit 112 asserts the signal during a plurality of successive periods in accordance with a duty cycle, e.g., as shown in FIG. 9. The time delay introduced into the signal by the delay circuit 110 is less than the time period during which the signal is continuously asserted, but greater than each of the time period(s) during which the signal is intermittently asserted. In this manner, the signal generated by the magnetic field sensing device 102 in response to sensing a magnetic field will prompt the microcontroller 64 to deactivate the IPG 14 during the normal mode, while never prompting the microcontroller 64 to deactivate the IPG 14 during the MRI-mode. Thus, if the time delay introduced into the signal is 200 ms, the time period during which the logic circuit 112 continuously asserts the signal is greater than 200 ms, and each of the time period(s) during which the logic circuit 112 intermittently asserts the signal will be less than 200 ms.

As one example in the case where the logic circuit 112 intermittently asserts the signal in accordance with a duty cycle, if the period of the duty cycle is 1 second, the assertion time period may be 100 ms, whereas the de-assertion time period may be 900 ms (i.e., a duty cycle of 10%). In this case, although the microcontroller 64 will only be able to sense the signal at the input terminal 106 ten percent of the time, this is sufficient when attempting to determine time and/or temperature at which an MRI is initiated or ceased within a one second accuracy. Of course, during the MRI-mode, the microcontroller 64 will not be able to sense the signal at the input terminal 108, since the logic circuit 100 will de-assert the signal before the delay circuit 100 outputs the signal to the input terminal 108.

In the embodiment illustrated in FIG. 7, the logic circuit 112 comprises a logic gate 114 (in this case, an AND-gate 114a) having a first input coupled to the output of the magnetic field sensing device 102, and a register 116 to which a second input of the logic gate 114 is coupled. Assuming that the signal output by the magnetic field sensing device 102 is a logic "0" when a magnetic field is sensed, the logic circuit 112 also includes a logic inverter 118 coupled between the first input of the AND-gate 114a and the output of the magnetic field sensing device 102. The logical inverter 118 inverts the logic "0" to a logical "1," which will prompt the microprocessor 64 to perform the afore-mentioned functions if and when it reaches the input terminals 106, 108. The register 116 stores either a signal assertion bit or a signal de-assertion bit under control of the microcontroller 64. In this case, the signal assertion bit is a logical "1" and the signal de-assertion bit is a logical "0." Thus, when the register 116 presents a logical "1" to the second input of the AND-gate 114a, a logical "1" presented by the inverter 114 to the first input will be passed to the output of the AND-gate 114a; in effect, asserting the signal output by the magnetic field sensing device 102. In contrast, when the register 116 presents a logical "0" to the second input of the AND-gate 114a, a logical "1" presented by the inverter 114 to the first input of the AND-gate 114a, is not passed to the output of the AND-gate 114a; in effect, de-asserting the signal output by the magnetic field sensing device 102. Thus, when the IPG 14 is in the normal mode, the microcontroller 64 will store a logical "1" (for a time period greater than the time delay of the delay circuit 110) in the register 116 to continuously assert the signal output by the magnetic field sensing device 102, and when the IPG 14 is in the MRI-mode, the microcontroller 64 will alternatively store a logical "1" (for a time period less than the time delay of the delay circuit 110) and a logical "0" in the register 110 to intermittently assert the signal output by the magnetic field sensing device 102.

Figure 8:
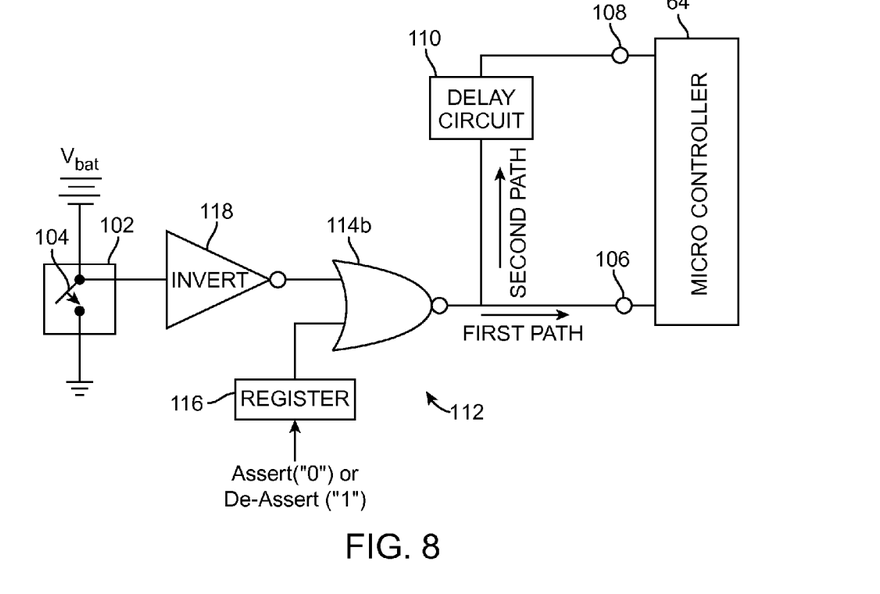
FIG. 8 is a block diagram illustrating the components of another embodiment of a magnetic field sensing assembly used in the IPG of FIGS. 4 and 5.

In an alternative embodiment illustrated in FIG. 8, the logic gate 114 takes the form of a NOR-gate, in which case, a logic inverter is not needed. The NOR-gate 114b has a first input coupled to the output of the magnetic field sensing device 102, and a second input coupled to the register 116. In this case, the signal assertion bit stored within the register 116 is a logical "0" and the signal de-assertion bit is a logical "1." Thus, when the register 116 presents a logical "0" to the second input of the NOR-gate 114b, a logical "0" presented by magnetic field sensing device 102 to the first input will be inverted and passed as a logical "1" to the output of the NOR-gate 114b; in effect, asserting the signal output by the magnetic field sensing device 102. In contrast, when the register 116 presents a logical "1" to the second input of the AND-gate 114a, a logical "0" presented by the magnetic field sensing device 102 to the first input of the NOR-gate 114b is inverted, but is passed as a logical "0" to the output of the NOR-gate 114b; in effect, de-asserting the signal output by the magnetic field sensing device 102. Thus, when the IPG 14 is in the normal mode, the microcontroller 64 will store a logical "0" (for a time period greater than the time delay of the delay circuit 110) in the register 116 to continuously assert the signal output by the magnetic field sensing device 102, and when the IPG 14 is in the MRI-mode, the microcontroller 64 will alternatively store a logical "0" (for a time period less than the time delay of the delay circuit 110) and a logical "1" in the register 110 to intermittently assert the signal output by the magnetic field sensing device.

Having described the structure and function of the SCS system 10, one technique for operating the system 10 between the normal mode, during which a conventional magnet can be used to inactivate the IPG 14, and an MRI-mode, during which the IPG 14 is prevented from being deactivated to allow the magnetic field generated by the MRI to be monitored, will now be described with reference to FIGS. 10 and 11.

Figure 10:
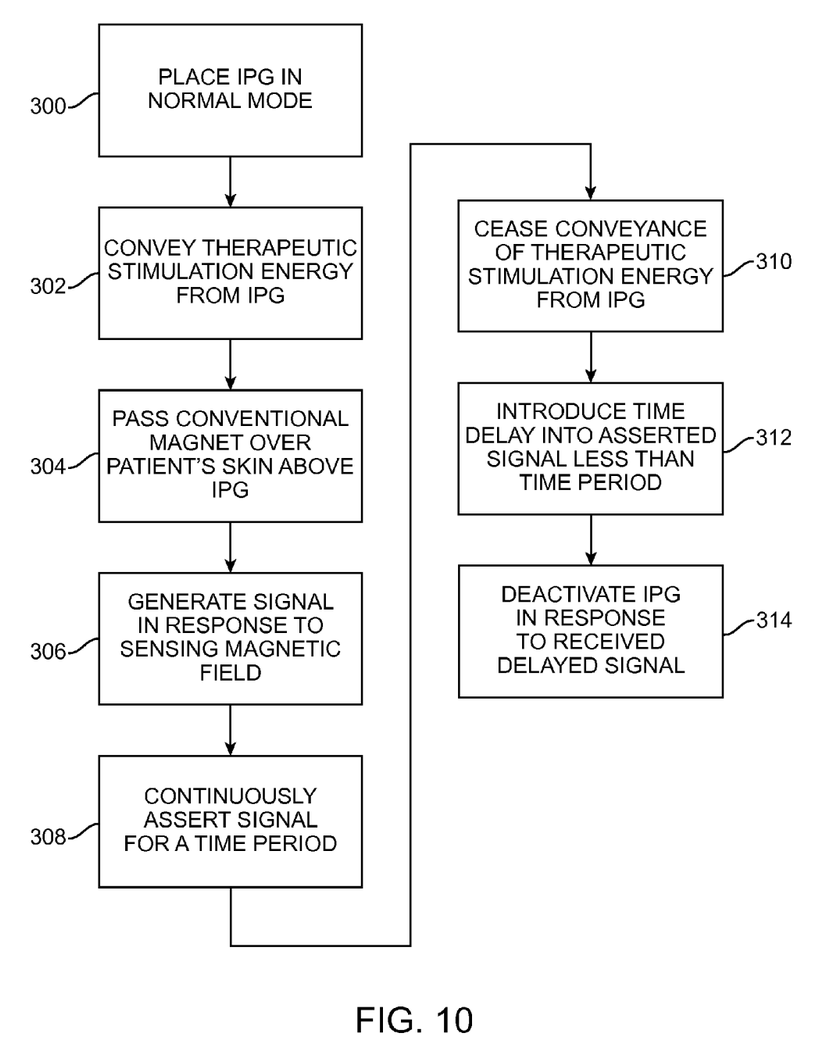
FIG. 10 is a flow diagram illustrating a technique used by the neurostimulation system of FIG. 2 to deactivate the IPG of FIGS. 4 and 5 when the IPG is in a normal mode.

Referring first to FIG. 10, if the IPG 14 is in the MRI-mode, the IPG 14 may be switched to the normal mode by transmitting a programming signal from the RC 16 and/or CP 18 to the IPG 14 (step 300). In this mode, electrical stimulation energy can be conveyed from the IPG 14 to the stimulation leads 12 in response to a programming signal received from the RC 16 and/or CP 18, thereby providing neurostimulation therapy to the patient (step 302). At any time during the normal mode, the patient may pass a conventional magnet over the patient's skin above the IPG 14 (step 304). In response, the magnetic field sensing device 102 generates a signal in response to sensing the magnetic field emitted by the conventional magnet (step 306), the logic circuit 112 continuously asserts the signal for a time period (step 308), and the delay circuit 110 introduces a time delay into the asserted signal less, with the time delay being less than the time period during which the signal is continuously asserted (step 310). The microcontroller 64, in response to the asserted signal, instructs the IPG 14 to cease conveyance of the electrical stimulation energy (step 312), and in response to the delayed asserted signal, deactivates the IPG 14 (step 314).

Figure 11:
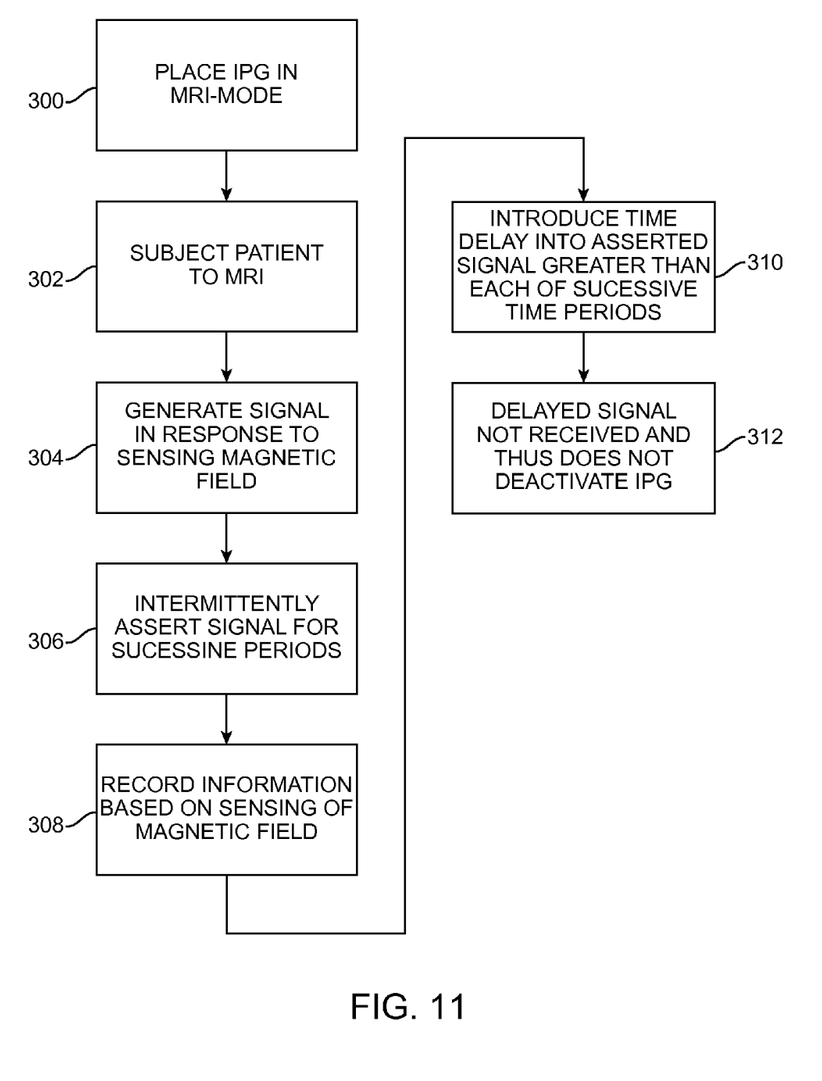
FIG. 11 is a flow diagram illustrating a technique used by the neurostimulation system of FIG. 2 to monitor a magnetic field while preventing deactivation of the IPG of FIGS. 4 and 5 when the IPG is in an MRI-mode.

Referring first to FIG. 11, if the IPG 14 is in the normal mode, the IPG 14 may be switched to the MRI-mode by transmitting a programming signal from the RC 16 and/or CP 18 to the IPG 14 (step 400). At any time during the MRI-mode, the patient may undergo an MRI (step 402). In response, the magnetic field sensing device 102 generates a signal in response to sensing the magnetic field emitted by the MRI scanning device (step 404), and the logic circuit 112 intermittently asserts the signal for at least one period, and preferably, during a plurality of successive periods (step 406). The microcontroller 64, in response to the asserted signal, monitors the magnetic field, e.g., by recording the time and/or temperature when the MRI is initiated and finished (step 408). The delay circuit 110 introduces a time delay into the asserted signal, with the time delay being greater than each of the successive time periods during which the signal is intermittently asserted (step 410). Because the time delay is greater than the each of the time periods in which the signal is intermittently asserted, the microcontroller 64 will not receive the delayed signal, and thus, will not deactivate the IPG 14 (step 412).

Although the afore-mentioned technique has been described in the context of an MRI, it should be appreciated that this technique can be used to monitor magnetic fields generated by any source while preventing deactivation of any implantable medical device by the magnetic field.

Although particular embodiments of the present inventions have been shown and described, it will be understood that it is not intended to limit the present inventions to the preferred embodiments, and it will be obvious to those skilled in the art that various changes and modifications may be made without departing from the spirit and scope of the present inventions. Thus, the present inventions are intended to cover alternatives, modifications, and equivalents, which may be included within the spirit and scope of the present inventions as defined by the claims.

What is claimed is:

1. An implantable medical device capable of being placed in a first operational mode and in a second operational mode, comprising:
   a magnetic field sensing device configured for outputting a signal in response to sensing a magnetic field;
   a logic circuit configured for receiving the signal from the magnetic field sensing device, wherein, in response to the signal from the magnetic field sensing device, the logic circuit is configured for continuously asserting the signal during a first time period when the medical device is in the first operational mode, and intermittently asserting the signal during at least one second time period when the medical device is in the second operational mode, wherein the first time period is greater than the second time period;
   a delay circuit configured for receiving the asserted signal from the logic circuit and introducing a time delay into the asserted signal, the time delay being less than the first time period, but greater than each of the at least one second time period; and
   control circuitry configured for receiving the delayed signal from the delay circuit and performing a function in response to receiving the delayed signal at a first input terminal.

2. The implantable medical device of claim 1, wherein the first operational mode is a normal mode, and the second operational mode is an MRI mode.

3. The implantable medical device of claim 1, wherein the function is deactivating the medical device.

4. The implantable medical device of claim 1, wherein the control circuitry is configured for performing another function in response to receiving the asserted signal at a second input terminal.

5. The implantable medical device of claim 4, wherein the other function cording information based on the sensed magnetic field.

6. The implantable medical device of claim 1, wherein the at least one second time period comprises a plurality of successive periods.

7. The implantable medical device of claim 6, wherein the logic circuit is configured for asserting the signal in accordance with a duty cycle.

8. The implantable medical device of claim 1, wherein the logic circuit comprises a logic gate and a register configured for storing a signal assertion bit, the logic gate having a first input coupled to the magnetic field sensing device, and a second input coupled to the register.

9. The implantable medical device of claim 8, wherein the logic gate is one of an AND-gate and a NOR-gate.

10. The implantable medical device of claim 1, wherein the magnetic field sensing device comprises one of a reed switch and a Hall sensor.

11. The implantable medical device of claim 1, wherein the time delay is in the range of 200 ms-400 ms.

12. The implantable medical device of claim 1, further comprising:
   a plurality of electrical terminals configured for being respectively coupled to a plurality of stimulation electrodes; and
   stimulation output circuitry configured for outputting electrical stimulation energy to the plurality of electrical terminals.

13. A method of operating a neurostimulation device implanted within a patient, comprising:
   when the neurostimulation device is in a first operational mode, generating a first signal in response to sensing a magnetic field by a magnetic field sensing device in the implanted neurostimulation device, continuously asserting the first signal, and introducing a time delay into the first asserted signal to generate a first delayed signal, wherein the time delay is less than a first time period, thereby prompting the neurostimulation device to deactivate in response to the first delayed signal; and
   when the neurostimulation device is in the second operational mode, generating a second signal in response to sensing a magnetic field by the magnetic field sensing device in the implanted neurostimulation device, intermittently asserting the second signal during at least one second time period, introducing a time delay into the second asserted signal to generate a second delayed signal, wherein the time delay is greater than each of the at least one second time period and the first time period is greater than the second time period, thereby preventing the neurostimulation device from deactivating in response to the second delayed signal.

14. The method of claim 13, wherein the neurostimulation device is placed in the first operational mode when the patient is not undergoing an MRI, and is placed in the second operational mode when the patient is undergoing an MRI.

15. The method of claim 13, further comprising performing another function in response to the second asserted signal when the neurostimulation device is in the second operational mode.

16. The method of claim 15, wherein the other function is recording information based on the sensed magnetic field.

17. The method of claim 13, wherein the at least one second time period comprises a plurality of successive periods.

18. The method of claim 17, wherein the second signal is intermittently asserted in accordance with a duty cycle.

19. The method of claim 13, wherein the time delay is in the range of 200 ms-400 ms.

* * * * *